United States Patent
Chiang et al.

(10) Patent No.: US 10,526,470 B2
(45) Date of Patent: Jan. 7, 2020

(54) METHOD FOR PRODUCING A WATER-SOLUBLE THERMALLY-CROSSLINKABLE POLYMERIC MATERIAL

(71) Applicant: Novartis AG, Basel (CH)

(72) Inventors: Chung-Yuan Chiang, Johns Creek, GA (US); Yongxing Qiu, Suwanee, GA (US); Kelly Kayi Tallau, Johns Creek, GA (US); Angela Driver-Scott, Atlanta, GA (US)

(73) Assignee: Novartis AG, Basel (CH)

( * ) Notice: Subject to any disclaimer, the term of this patent is extended or adjusted under 35 U.S.C. 154(b) by 191 days.

(21) Appl. No.: 15/704,176

(22) Filed: Sep. 14, 2017

(65) Prior Publication Data

US 2018/0079889 A1    Mar. 22, 2018

Related U.S. Application Data

(60) Provisional application No. 62/396,843, filed on Sep. 20, 2016.

(51) Int. Cl.

| | |
|---|---|
| *C08K 5/3412* | (2006.01) |
| *C08K 5/00* | (2006.01) |
| *C08G 73/02* | (2006.01) |
| *C07D 205/04* | (2006.01) |
| *C08G 65/08* | (2006.01) |
| *C08K 3/32* | (2006.01) |
| *C08L 79/00* | (2006.01) |
| *C08L 71/02* | (2006.01) |
| *B29D 11/00* | (2006.01) |
| *C08G 73/00* | (2006.01) |
| *C09D 4/00* | (2006.01) |

(52) U.S. Cl.
CPC ........ *C08K 5/3412* (2013.01); *C07D 205/04* (2013.01); *C08G 73/022* (2013.01); *C08K 5/0025* (2013.01); *C08G 65/08* (2013.01)

(58) Field of Classification Search
None
See application file for complete search history.

(56) References Cited

U.S. PATENT DOCUMENTS

| | | |
|---|---|---|
| 3,408,429 A | 10/1968 | Otto |
| 4,347,198 A | 8/1982 | Ohkada |
| 5,461,433 A | 10/1995 | Nakabayashi et al. |
| 5,508,317 A | 4/1996 | Mueller |
| 5,583,463 A | 12/1996 | Merritt |
| 5,789,464 A | 8/1998 | Mueller |
| 5,849,810 A | 12/1998 | Mueller |
| 6,218,508 B1 | 4/2001 | Kragh et al. |
| 8,529,057 B2 | 9/2013 | Qiu et al. |
| 2012/0026457 A1* | 2/2012 | Qiu .................... G02B 1/043 351/159.33 |
| 2012/0026458 A1 | 2/2012 | Qiu et al. |
| 2012/0314185 A1 | 12/2012 | Bauman et al. |
| 2013/0118127 A1 | 5/2013 | Kolluru et al. |
| 2013/0337160 A1* | 12/2013 | Holland ............ C09D 139/04 427/162 |
| 2016/0061995 A1 | 3/2016 | Chang |
| 2016/0326046 A1 | 11/2016 | Quinter et al. |
| 2017/0068018 A1 | 3/2017 | Qian et al. |
| 2017/0068019 A1 | 3/2017 | Qian et al. |
| 2017/0165932 A1 | 6/2017 | Qian et al. |
| 2018/0079157 A1 | 3/2018 | Tucker et al. |
| 2018/0079158 A1 | 3/2018 | Qiu et al. |
| 2018/0081197 A1 | 3/2018 | Qiu et al. |
| 2018/0113236 A1 | 4/2018 | Bothe et al. |
| 2018/0120590 A1 | 5/2018 | Bothe |

FOREIGN PATENT DOCUMENTS

| | | |
|---|---|---|
| EP | 1465931 B1 | 8/2007 |
| WO | 2014/093299 A1 | 6/2014 |

* cited by examiner

*Primary Examiner* — Randy P Gulakowski
*Assistant Examiner* — Ha S Nguyen
(74) *Attorney, Agent, or Firm* — Jian Zhou

(57) ABSTRACT

The invention is related to a cost-effective method for producing water-soluble thermally-crosslinkable hydrophilic polymeric materials. Resultant materials can find particular use in preparing a packaging solution used for packaging and autoclaving medical devices, especially contact lenses. Those packaging solutions are especially suitable for forming a relatively-thick and soft hydrogel coatings on contact lenses or medical devices according to an in-package-crosslinking (IPC) processes. The resultant non-silicone hydrogel coatings can have a superior lubricity (a friction rating of 0) with minimized or no surface cracking.

16 Claims, No Drawings

METHOD FOR PRODUCING A WATER-SOLUBLE THERMALLY-CROSSLINKABLE POLYMERIC MATERIAL

This application claims the benefit under 35 USC § 119(e) of U.S. provisional application No. 62/396,843 filed 20 Sep. 2016, herein incorporated by reference in its entirety.

The present invention generally relates to a method for producing a water-soluble, thermally-crosslinkable polymeric material.

BACKGROUND

A new class of soft contact lenses, water gradient silicone hydrogel contact lenses, have been developed and successfully introduced in the market. This new class of silicone hydrogel contact lenses is characterized by having a water-gradient structural configuration, an increase from 33% to over 80% water content from core to surface. This unique design delivers a highly-lubricious and extremely-soft lens surface. Such soft contact lenses can be produced according to a cost-effective approach that is described in U.S. Pat. No. 8,529,057 (herein incorporated by reference in its entirety) and involves a step of crosslinking and covalently attaching of a water-soluble highly-branched hydrophilic polymeric material onto lens surfaces to form surface gels.

According to U.S. Pat. No. 8,529,057, a water-soluble highly-branched hydrophilic polymeric material is prepared by partially reacting a polyamidoamine-epichlorohydrin (PAE) with a wetting agent, at various concentration ratio of PAE to the wetting agent and at a reaction temperature for a given reaction time, to achieve a desired lubricity of the surface gels while minimizing or eliminating surface defects (e.g., surface cracking, etc.). However, methods described in U.S. Pat. No. 8,529,057 may not be efficient, as it requires a relatively long reaction time (i.e., at a higher production cost) and/or a relatively-larger amount of a wetting agent. The relatively long reaction time and excessive amount of a wetting agent (especially a relatively expansive wetting agent) can increase the production cost.

Therefore, there is still a need for developing a cost-effective method for producing water-soluble highly-branched hydrophilic polymeric material useful for producing water gradient contact lenses.

SUMMARY OF THE INVENTION

The invention, in one aspect, provides a method for producing a water-soluble thermally-crosslinkable polymeric material, the method of invention comprising the steps of: (1) obtaining a reactive mixture which is an aqueous solution comprising (a) an azetidinium-containing polymer having azetidinium groups, (b) a hydrophilicity-enhancing agent (i.e., a wetting agent) having at least one reactive functional group selected from the group consisting of primary amino group, secondary amino group, carboxyl group, thiol group, and a combination thereof, and (c) one or more non-polymeric ionic compounds, provided that the aqueous solution either has a pH of at least 8.0 and/or that the non-polymeric ionic compounds are present in the aqueous solution in a total amount of (i) 0 to about 135 mM (millimolars) if the hydrophilicity-enhancing agent is non-ionic or positively-charged at the pH of the aqueous solution or (ii) from about 20 mM to about 135 mM if the hydrophilicity-enhancing agent is negatively-charged at the pH of the aqueous solution; and (2) heating the reactive mixture to reach a reaction temperature of from about 40° C. to about 85° C. and maintaining the temperature of the reactive mixture at the reaction temperature for a time period to obtain the water-soluble thermally-crosslinkable polymeric material in which the hydrophilicity-enhancing agent is covalently attached to the azetidinium-containing polymer through one or more covalent linkages each formed between one azetidinium group and one reactive functional group, wherein the water-soluble thermally-crosslinkable polymeric material comprises azetidinium groups.

This and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be affected without departing from the spirit and scope of the novel concepts of the disclosure.

DETAILED DESCRIPTION OF EMBODIMENTS OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well-known and commonly employed in the art.

"Contact Lens" refers to a structure that can be placed on or within a wearer's eye. A contact lens can correct, improve, or alter a user's eyesight, but that need not be the case. A contact lens can be of any appropriate material known in the art or later developed, and can be a soft lens, a hard lens, or a hybrid lens. A "silicone hydrogel contact lens" refers to a contact lens comprising a silicone hydrogel bulk (core) material. A person skilled in the art knows very well how to make contact lenses (either non-silicone hydrogel contact lenses or silicone hydrogel contact lenses). For example, contact lenses can be produced in a conventional "spin-casting mold," as described for example in U.S. Pat. No. 3,408,429, or by the full cast-molding process in a static form, as described in U.S. Pat. Nos. 4,347,198; 5,508,317; 5,583,463; 5,789,464; and 5,849,810, or by lathe cutting of buttons as used in making customized contact lenses.

A "soft contact lens" refers to a contact lens which has an elastic modulus (i.e., Young's modulus) of less than 2.5 MPa.

A "hydrogel" or "hydrogel material" refers to a crosslinked polymeric material which has three-dimensional polymer networks (i.e., polymer matrix), is insoluble in water, but can hold at least 10 percent by weight of water in its polymer matrix when it is fully hydrated.

A "silicone hydrogel" refers to a silicone-containing hydrogel obtained by copolymerization of a polymerizable composition comprising at least one silicone-containing monomer or at least one silicone-containing macromer or at least one crosslinkable silicone-containing prepolymer.

As used in this application, the term "non-silicone hydrogel" refers to a hydrogel that is theoretically free of silicon.

"Hydrophilic," as used herein, describes a material or portion thereof that will more readily associate with water than with lipids.

"Surface hydrophilicity", as used herein, describes a surface property that represents the extent to which a surface interacts with water, as measured by water-break-up-time (WBUT). The higher the value of WBUT is, the higher the surface hydrophilicity is.

In accordance with the invention, the "surface lubricity" of a contact lens (or a medical device) is measured by a friction rating which is a number from 0 to 4. The higher the value of friction rating is, the lower the surface lubricity is.

A "vinylic monomer" refers to a compound that has one sole ethylenically unsaturated group, is soluble in a solvent, and can be polymerized actinically or thermally.

The term "soluble", in reference to a compound or material in a solvent, means that the compound or material can be dissolved in the solvent to give a solution with a concentration of at least about 0.05% by weight at room temperature (i.e., a temperature of about 22° C. to about 28° C.). The term "water-soluble", in reference to a compound or material in water, means that the compound or material can be dissolved in water to give a solution with a concentration of at least about 0.05% by weight at room temperature The term "insoluble", in reference to a compound or material in a solvent, means that the compound or material can be dissolved in the solvent to give a solution with a concentration of less than 0.005% by weight at room temperature (as defined above).

As used in this application, the term "ethylenically unsaturated group" is employed herein in a broad sense and is intended to encompass any groups containing at least one >C=C<group. Exemplary ethylenically unsaturated groups include without limitation (meth)acryloyl

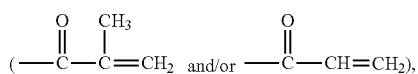

allyl, vinyl, styrenyl, or other C=C containing groups.

The term "(meth)acrylamide" refers to methacrylamide and/or acrylamide.

The term "(meth)acrylate" refers to methacrylate and/or acrylate.

A "hydrophilic vinylic monomer", as used herein, refers to a vinylic monomer which as a homopolymer typically yields a polymer that is water-soluble or can absorb at least 10 percent by weight of water.

A "hydrophobic vinylic monomer", as used herein, refers to a vinylic monomer which as a homopolymer typically yields a polymer that is insoluble in water and can absorb less than 10 percent by weight of water.

A "macromer" or "prepolymer" refers to a compound or polymer that contains ethylenically unsaturated groups and has an average molecular weight of greater than 700 Daltons.

As used in this application, the term "vinylic crosslinker" refers to a compound having at least two ethylenically unsaturated groups. A "vinylic crosslinking agent" refers to a vinylic crosslinker having a molecular weight of 700 Daltons or less.

As used in this application, the term "polymer" means a material formed by polymerizing/crosslinking one or more monomers or macromers or prepolymers or combinations thereof.

As used in this application, the term "molecular weight" of a polymeric material (including monomeric or macromeric materials) refers to the number-average molecular weight unless otherwise specifically noted or unless testing conditions indicate otherwise.

The term "alkyl" refers to a monovalent radical obtained by removing a hydrogen atom from a linear or branched alkane compound. An alkyl group (radical) forms one bond with one other group in an organic compound.

The term "alkylene divalent group" or "alkylene diradical" or "alkyl diradical" interchangeably refers to a divalent radical obtained by removing one hydrogen atom from an alkyl. An alkylene divalent group forms two bonds with other groups in an organic compound.

The term "alkyl triradical" refers to a trivalent radical obtained by removing two hydrogen atoms from an alkyl. An alkyl triradical forms three bonds with other groups in an organic compound.

The term "alkoxy" or "alkoxyl" refers to a monovalent radical obtained by removing the hydrogen atom from the hydroxyl group of a linear or branched alkyl alcohol. An alkoxy group (radical) forms one bond with one other group in an organic compound.

In this application, the term "substituted" in reference to an alkyl diradical or an alkyl radical means that the alkyl diradical or the alkyl radical comprises at least one substituent which replaces one hydrogen atom of the alkyl diradical or the alkyl radical and is selected from the group consisting of hydroxy (—OH), carboxy (—COOH), —NH$_2$, sulfhydryl (—SH), $C_1$-$C_4$ alkyl, $C_1$-$C_4$ alkoxy, $C_1$-$C_4$ alkylthio (alkyl sulfide), $C_1$-$C_4$ acylamino, $C_1$-$C_4$ alkylamino, di-$C_1$-$C_4$ alkylamino, halogen atom (Br or Cl), and combinations thereof.

In this application the term "azetidinium" or "3-hydroxyazetidinium" refers to a positively-charged, divalent radical (or group or moiety) of

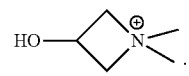

The term "azlactone" refers to a mono-valent radical of formula

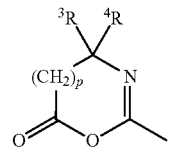

in which p is 0 or 1; $^3R$ and $^4R$ independently of each other is $C_1$-$C_8$ alkyl (preferably methyl).

As used in this application, the term "phosphorylcholine" refers to a monovalent zwitterionic group of

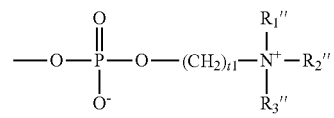

in which t1 is an integer of 1 to 5 and $R_1''$, $R_2''$ and $R_3''$ independently of one another are $C_1$-$C_8$ alkyl or $C_1$-$C_8$ hydroxyalkyl.

In this application, an "oxazoline" refers to a compound of

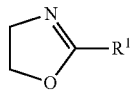

in which $R^1$ is hydrogen, $C_1$-$C_{18}$ alkyl, $C_1$-$C_4$ alkyl-substituted phenyl, $C_1$-$C_4$-alkoxy-substituted phenyl, $C_6$-$C_{18}$ aryl radical, N-pyrrolidonyl-$C_1$-$C_4$ alkyl, a monovalent radical of -alk-$(OC_2H_4)_{m3}$—OR" (in which alk is $C_1$-$C_6$ alkyl diradical, R" is $C_1$-$C_4$ alkyl, preferably methyl, and m3 is an integer from 1 to 10 (preferably 1 to 5)), preferably R1 is methyl, ethyl, propyl, N-pyrrolidonyl-$C_1$-$C_4$ alkyl, a monovalent radical of -alk-$(OC_2H_4)_{m3}$—OR" (in which alk is $C_1$-$C_6$ alkyl diradical, R" is $C_1$-$C_4$ alkyl, preferably methyl, and m3 is an integer from 1 to 10 (preferably 1 to 5)).

In this application, the term "polyoxazoline" refers to a linear polymer having a formula of

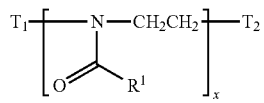

in which: $T_1$ and $T_2$ are two terminal groups; $R^1$ is hydrogen, methyl, ethyl, N-pyrrolidonylmethyl, N-pyrrolidonylethyl, N-pyrrolidonylpropyl, or a monovalent radical of -alk-$(OC_2H_4)_{m3}$—OR in which alk is $C_1$-$C_4$ alkyl diradical; R" is $C_1$-$C_4$ alkyl (preferably methyl); m3 is an integer from 1 to 10 (preferably 1 to 5); x is an integer from 5 to 500. A polyoxazoline segment has a divalent polymer chain of a formula of

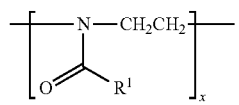

in which $R^1$ and x are as defined above.

In this application, the term "poly(2-oxazoline-co-ethyleneimine)" refers to a statistical copolymer having a formula of

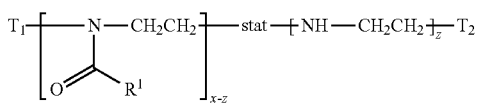

in which: $T_1$ and $T_2$ are terminal groups; $R^1$ is hydrogen, methyl, ethyl, N-pyrrolidonylmethyl, N-pyrrolidonylethyl, N-pyrrolidonylpropyl, or a monovalent radical of -alk-$(OC_2H_4)_{m3}$—OR" in which alk is $C_1$-$C_4$ alkyl diradical; R" is $C_1$-$C_4$ alkyl (preferably methyl); m3 is an integer from 1 to 10 (preferably 1 to 5); x is an integer from 5 to 500; z is an integer equal to or less than x. A poly(2-oxazoline-co-ethyleneimine) is obtained by hydrolyzing a polyoxazoline.

In this application, the term "poly(2-oxazoline-co-ethyleneimine)-epichlorohydrin" refers to a polymer obtained by reacting a poly(2-oxazoline-co-ethyleneimine) with epichlorohydrin to convert all or substantial percentage (≥90%) of the secondary amine groups of the poly(2-oxazoline-co-ethyleneimine) into azetidinium groups. Examples of poly (2-oxazoline-co-ethyleneimine)-epichlorohydrin are disclosed in U.S. pat. Appl. pub. No. 2016/0061995 A1 (herein incorporated by reference in its entirety).

An "epichlorohydrin-functionalized polyamine" or "epichlorohydrin-functionalized polyamidoamine" refers to a polymer obtained by reacting a polyamine or polyamidoamine with epichlorohydrin to convert all or a substantial percentage of the secondary amine groups of the polyamine or polyamidoamine into azetidinium groups.

The term "polyamidoamine-epichlorohydrin" refers to an epichlorohydrin-functionalized adipic acid-diethylenetriamine copolymer.

The term "thermally-crosslinkable" in reference to a polymeric material or a functional group means that the polymeric material or the functional group can undergo a crosslinking (or coupling) reaction with another material or functional group at a relatively-elevated temperature (from about 40° C. to about 140° C.), whereas the polymeric material or functional group cannot undergo the same crosslinking reaction (or coupling reaction) with another material or functional group at room temperature (i.e., from about 22° C. to about 28° C., preferably from about 24° C. to about 26° C., in particular at about 25° C.) to an extend detectable for a period of about one hour.

As used in this application, the term "reactive vinylic monomer" refers to any vinylic monomer having at least one reactive functional group selected from the group consisting of carboxyl group, primary amino group, and secondary amino group.

As used in this application, the term "non-reactive vinylic monomer" refers to any vinylic monomer (either hydrophilic or hydrophobic vinylic monomer) free of carboxyl group, primary amino group, secondary amino group, epoxide group, isocyanate group, azlactone group, or aziridine group.

A free radical initiator can be either a photoinitiator or a thermal initiator. A "photoinitiator" refers to a chemical that initiates free radical crosslinking/polymerizing reaction by the use of light. A "thermal initiator" refers to a chemical that initiates radical crosslinking/polymerizing reaction by the use of heat energy.

A "water contact angle" refers to an average water contact angle (i.e., contact angles measured by Sessile Drop method) at the room temperature, which is obtained by averaging measurements of contact angles with at least 3 individual contact lenses.

The term "intactness" in reference to a coating on a silicone hydrogel contact lens is intended to describe the extent to which the contact lens can be stained by Sudan Black in a Sudan Black staining test described in Example 1. Good intactness of the coating on a silicone hydrogel contact lens means that there is practically no Sudan Black staining of the contact lens.

The term "durability" in reference to a coating on a silicone hydrogel contact lens is intended to describe that the coating on the silicone hydrogel contact lens can survive a desired number of cycles of manual rubbing.

The term "modulus" or "elastic modulus" in reference to a contact lens or a material means the tensile modulus or Young's modulus which is a measure of the stiffness of a contact lens or a material. The modulus can be measured using a method in accordance with ANSI Z80.20 standard. A person skilled in the art knows well how to determine the elastic modulus of a silicone hydrogel material or a contact lens. For example, all commercial contact lenses have reported values of elastic modulus.

An "aqueous solution" or a "water-based solution" interchangeably refers to a solution which is a homogeneous mixture consisting of a water-based solvent and one or more solutes dissolved in the water-based solvent. A "water-based solvent" is intended to describe a solvent system which consists of at least 50% (preferably at least about 60%, more preferably at least about 80%, even more preferably at least about 90%, in particular at least about 95%) by weight of water and at most 50% (preferably about 40% or less, more preferably about 20% or less, even more preferably about 10% or less, in particular about 5% or less) by weight of one or more organic solvents relative to the weight of the solvent system. An aqueous coating solution refers to an aqueous solution containing at least one polymeric coating material as a solute in the solution.

An "organic-based solution" refers to a solution which is a homogeneous mixture consisting of an organic-based solvent and one or more solutes dissolved in the organic based solvent. An "organic-based solvent" is intended to describe a solvent system which consists of one or more organic solvents and less than 49%, preferably about 40% or less, more preferably about 20% or less, even more preferably about 10% or less, in particular about 5% or less by weight of water relative to the weight of the solvent system. An organic-based coating solution refers to an organic-based solution containing at least one polymeric coating material as a solute in the solution.

An "in-package-crosslinking process" or "IPC process" refers to a crosslinking reaction carried out in-situ directly in a packaging solution in a package (which is for storing and sterilizing a contact lens or a medical device) during autoclave. Examples of such processes are described in U.S. Pat. No. 8,529,057 (herein incorporated by reference in its entirety). A non-silicone hydrogel coating can be formed on a medical device or a contact lens.

The invention is generally related to an efficient method for producing water-soluble thermally-crosslinkable polymeric material useful for producing water gradient contact lenses from an aqueous reactive mixture including an azetidinium-containing polymer and a reactive hydrophilicity-enhancing agent having at least one carboxyl, primary or secondary amino or thiol group. It is discovered here that by carefully selecting the pH of the aqueous reactive mixture and/or the total concentration of non-polymeric ionic compounds (e.g., salts used as tonicity agents, buffering agents, or the like), one can control the rate and extent of the thermally-induced reaction (shown in scheme I) between one azetidinium group and one reactive functional group (i.e., carboxyl, primary or secondary amino or thiol group). With such a controllability, a resultant water-soluble thermally-crosslinkable polymeric material can be obtained to have a desired azetidinium concentration and a desired concentration of cross linkages formed between the azetidinium-containing polymer and a reactive hydrophilicity-enhancing agent, so that it can be used in forming a hydrogel coating surface having a superior lubricity (a friction rating of 0) with minimized or no surface cracking.

Scheme I

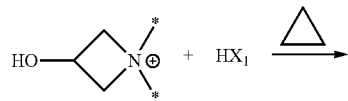

-continued

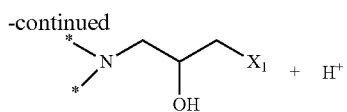

in which $X_1$ is —S—*, —OC(=O)—*, or —NR'—* in which R' is hydrogen or a $C_1$-$C_{20}$ unsubstituted or substituted alkyl group, and * represents an organic radical.

It is believed that higher pH of aqueous reactive mixture would render an azetidinium-containing polymer more reactive by opening up the azetidinium group more readily and thereby could shorten the reaction time required for preparing a water-soluble thermally-crosslinkable polymeric material and/or enhancing the reaction rate between one azetidinium group and one reactive functional group. It is also believed that the total concentration of non-polymeric ionic compounds in the aqueous reactive mixture can also affect the thermally induced reaction between an azetidinium group and a reactive functional group shown in Scheme I. For example, a reduced total concentration of non-polymeric ionic compounds (e.g., NaCl and buffering agents) in the pre-reaction mixture could reduce shielding effect of the charge interaction between positively-charged azetidinium groups and negatively-charged carboxyl groups, therefore enhancing the reaction between an azetidinium-containing polymer and a hydrophilicity enhancing agent having carboxyl groups (e.g., poly(acrylamide-co-acrylic acid), or the like). The advantages associated with a method of the invention is a relatively-short reaction time to save the production cost, an efficient reaction to use a smaller amount of an expensive hydrophilicity-enhancing agent, a better reaction controllability in the concentrations of azetidinium groups and covalent linkages in the water-soluble thermally-crosslinkable polymeric material suitable for forming a surface hydrogel with better lubricity and minimal or no surface cracking.

The invention, in one aspect, provides a method for producing a water-soluble thermally-crosslinkable polymeric material, the method of invention comprising the steps of:

(1) obtaining a reactive mixture which is an aqueous solution comprising
 (a) an azetidinium-containing polymer having azetidinium groups,
 (b) a hydrophilicity-enhancing agent (i.e., a wetting agent) having at least one reactive functional group selected from the group consisting of primary amino group, secondary amino group, carboxyl group, thiol group, and a combination thereof, and
 (c) one or more non-polymeric ionic compounds, provided that the aqueous solution either has a pH of at least 8.0 (preferably at least 8.5, more preferably at least 9.0) and/or that the non-polymeric ionic compounds are present in the aqueous solution in a total amount of (i) 0 mM to about 135 mM (preferably about 0.5 mM to about 130 mM, more preferably from about 1 mM to about 120 mM) if the hydrophilicity-enhancing agent is non-ionic or positively-charged at the pH of the aqueous solution or (ii) from about 20 millimolars (mM) to about 135 mM (preferably about 25 mM to about 130 mM, more preferably from about 30 mM to about 120 mM) if the hydrophilicity-enhancing agent is negatively-charged charged at the pH of the aqueous solution; and (2) heating the reactive mixture to reach a reaction temperature of from about 40° C. to about 85° C. and maintaining the temperature of the reactive mixture at the reaction temperature for a time period to obtain the water-soluble thermally-crosslinkable polymeric material in which the hydrophilicity-enhancing agent is covalently attached to the azetidinium-containing polymer through one or more covalent linkages each formed between one azetidinium group and one reactive functional group, wherein the water-soluble thermally-crosslinkable polymeric material comprises azetidinium groups.

Any suitable azetidinium-containing polymers can be used in the invention. Examples of azetidinium-containing polymers includes without limitation epichlorohydrin-functionalized polyamines, homopolymers of an azetidinium-containing vinylic monomer, copolymers of an azetidinium-containing vinylic monomer with one or more vinylic monomers.

Preferably, an azetidinium-containing polymer is an epichlorohydrin-functionalized polyamine. An epichlorohydrin-functionalized polyamine can be obtained by reacting epichlorohydrin with a polyamine polymer or a polymer containing secondary amino groups. For example, a poly (alkylene imines) or a poly(amidoamine) which is a polycondensate derived from a polyamine and a dicarboxylic acid (e.g., adipic acid-diethylenetriamine copolymers) can react with epichlorohydrin to form an epichlorohydrin-functionalized polymer; a homopolymer or copolymer of mono-alkylaminoalkyl (meth)acrylate or mono-alkylaminoalkyl (meth)acrylamide can also react with epichlorohydrin to form an epichlorohydrin-functionalized polyamine; a poly(2-oxazoline-co-ethyleneimine) copolymer can react with epichlorohydrin to form an epichlorohydrin-functionalized polyamine (i.e., a poly(2-oxazoline-co-ethyleneimine)-epichlorohydrin). The reaction conditions for epichlorohydrin-functionalization of a polyamine or polyamidoamine polymer are taught in EP1465931 (herein incorporated by reference in its entirety). A preferred epichlorohydrin-functionalized polyamine is polyamidoamine-epichlorohydrin (PAE) or a poly(2-oxazoline-co-ethyleneimine)-epichlorohydrin.

Polyamidoamine-epichlorohydrin is commercially available, such as, for example, Kymene® or Polycup® resins (epichlorohydrin-functionalized adipic acid-diethylenetriamine copolymers) from Hercules.

Poly(2-oxazoline-co-ethyleneimine)-epichlorohydrin can be prepared according to procedures described in U.S. Pat. Appl. Pub. No. 2016/0061995 A1 (herein incorporated by reference in its entirety).

Homopolymers and copolymers of an azetidinium-containing vinylic monomer can be obtained according to the procedures described in U.S. Pat. Appl. Pub. No. 2012/0337160A1 (herein incorporated by reference in its entirety).

Any suitable hydrophilicity-enhancing agents can be used in the invention so long as they are ophthalmically compatible and contain at least one primary or secondary amino group, at least one carboxyl group, and/or at least one thiol group.

A preferred class of hydrophilicity-enhancing agents include without limitation: primary amino-, secondary amino-, carboxyl- or thiol-containing monosaccharides (e.g., 3-amino-1,2-propanediol, 1-thiolglycerol, 5-keto-D-gluconic acid, galactosamine, glucosamine, galacturonic acid, gluconic acid, glucosaminic acid, mannosamine, saccharic acid 1,4-lactone, saccharide acid, Ketodeoxynonulosonic acid, N-methyl-D-glucamine, 1-amino-1-deoxy-β-D-galactose, 1-amino-1-deoxysorbitol, 1-methylamino-1-deoxysorbitol, N-aminoethyl gluconamide); primary amino-, secondary amino-, carboxyl- or thiol-containing disaccharides (e.g., chondroitin disaccharide sodium salt, di(β-D-xylopyranosyl)amine, digalacturonic acid, heparin disaccharide, hyaluronic acid disaccharide, Lactobionic acid); and primary amino-, secondary amino-, carboxyl- or thiol-containing oligosaccharides (e.g., carboxymethyl-β-cyclodextrin sodium salt, trigalacturonic acid); and combinations thereof.

Another preferred class of hydrophilicity-enhancing agents is hydrophilic polymers having one or more (primary or secondary) amino, carboxyl and/or thiol groups. More preferably, the content of the amino (—NHR' with R' as defined above), carboxyl (—COOH) and/or thiol (—SH) groups in a hydrophilic polymer as a hydrophilicity-enhancing agent is less than about 40%, preferably less than about 30%, more preferably less than about 20%, even more preferably less than about 10%, by weight based on the total weight of the hydrophilic polymer.

One preferred class of hydrophilic polymers as hydrophilicity-enhancing agents are (primary or secondary) amino- or carboxyl-containing polysaccharides, for example, such as, carboxymethylcellulose (having a carboxyl content of about 40% or less, which is estimated based on the composition of repeating units, —[$C_6H_{10-m}O_5(CH_2CO_2H)_m$]— in which m is 1 to 3), carboxyethylcellulose (having a carboxyl content of about 36% or less, which is estimated based on the composition of repeating units, —[$C_6H_{10-m}O_5(C_2H_4CO_2H)_m$]— in which m is 1 to 3) carboxypropylcellulose (having a carboxyl content of about 32% or less, which is estimated based on the composition of repeating units, —[$C_6H_{10-m}O_5(C_3H_6CO_2H)_m$]—, in which m is 1 to 3), hyaluronic acid (having a carboxyl content of about 11%, which is estimated based on the composition of repeating units, —($C_{13}H_{20}O_9NCO_2H$)—), chondroitin sulfate (having a carboxyl content of about 9.8%, which is estimated based on the composition of repeating units, —($C_{12}H_{18}O_{13}NS CO_2H$)—), or combinations thereof.

Another preferred class of hydrophilic polymers as hydrophilicity-enhancing agents include without limitation: poly (ethylene glycol) (PEG) with mono-amino (primary or secondary amino), carboxyl or thiol group (e.g., PEG-NH$_2$, PEG-SH, PEG-COOH); H$_2$N-PEG-NH$_2$; HOOC-PEG-COOH; HS-PEG-SH; H$_2$N-PEG-COOH; HOOC-PEG-SH; H$_2$N-PEG-SH; multi-arm PEG with one or more amino (primary or secondary), carboxyl or thiol groups; PEG dendrimers with one or more amino (primary or secondary), carboxyl or thiol groups; a diamino-(primary or secondary) or dicarboxyl-terminated homo- or co-polymer of a non-reactive hydrophilic vinylic monomer; a monoamino-(primary or secondary) or monocarboxyl-terminated homo- or co-polymer of a non-reactive hydrophilic vinylic monomer; a copolymer which is a polymerization product of a composition comprising (1) about 60% by weight or less, preferably from about 0.1% to about 30%, more preferably from about 0.5% to about 20%, even more preferably from about 1% to about 15%, by weight of one or more reactive vinylic monomers and (2) at least one non-reactive hydrophilic vinylic monomer; and combinations thereof.

In accordance with the invention, reactive vinylic monomers can be carboxyl-containing vinylic monomers, primary amino-containing vinylic monomers, or secondary amino-containing vinylic monomers.

Examples of preferred carboxyl-containing vinylic monomers include without limitation acrylic acid, $C_1$-$C_4$ alkylacrylic acid (e.g., methacrylic ethylacrylic acid, propylacrylic acid, butylacrylic acid), N-2-acrylamidoglycolic acid, beta methyl-acrylic acid (crotonic acid), alpha-phenyl acrylic acid, beta-acryloxy propionic acid, sorbic acid, angelic acid, cinnamic acid, 1-carobxy-4-phenyl butadiene-1,3, itaconic acid, citraconic acid, mesaconic acid, glutaconic acid, aconitic acid, maleic acid, fumaric acid, tricarboxy ethylene, and combinations thereof.

Examples of preferred primary and secondary amino-containing vinylic monomers include without limitation amino-$C_2$-$C_6$ alkyl (meth)acrylate, $C_1$-$C_6$ alkylamino-$C_2$-$C_6$ alkyl (meth)acrylate, allylamine, vinylamine, amino-$C_2$-$C_6$ alkyl (meth)acrylamide, $C_1$-$C_6$ alkylamino-$C_2$-$C_6$ alkyl (meth)acrylamide, and combinations thereof.

In accordance with the invention, a non-reactive vinylic monomer is a vinylic monomer free of any carboxyl group, primary amino group, secondary amino group, epoxide group, isocyanate group, azlactone group, or aziridine group. Non-reactive vinylic monomers preferably are hydrophilic vinylic monomers, phosphorylcholine-containing vinylic monomers, or combinations thereof. Examples of preferred non-reactive hydrophilic vinylic monomers include without limitation (meth)acrylamide, N,N-dimethyl (meth)acrylamide, N-vinylpyrrolidone (NVP), N-vinyl formamide, N-vinyl acetamide, N-vinyl isopropylamide, N-vinyl-N-methyl acetamide, N,N-dimethylaminoethyl (meth) acrylate, N,N-dimethylaminopropyl (meth)acrylamide, glycerol (meth)acrylate, 3-(meth)acryloylamino-1-propanol, N-hydroxyethyl (meth)acrylamide, N-hydroxypropyl (meth)acrylamide, N-[tris(hydroxymethyl)methyl]-acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 2-hydroxyethyl (meth)acrylate, hydroxypropyl (meth)acrylate, $C_1$-$C_4$-alkoxy polyethylene glycol (meth)acrylate having a weight average molecular weight of up to 1500 Daltons, allyl alcohol, vinyl alcohol, and combinations thereof.

Examples of preferred non-reactive phosphorylcholine-containing vinylic monomers include without limitation (meth)acryloyloxyethyl phosphorylcholine (aka, MPC, or 2-((meth)acryloyloxy)ethyl-2'-(trimethylammonio)ethylphosphate), (meth)acryloyloxypropyl phosphorylcholine (aka, 3-((meth)acryloyloxy)propyl-2'-(trimethylammonio) ethylphosphate), 4-((meth)acryloyloxy)butyl-2'-(trimethylammonio)ethylphosphate, 2-[(meth)acryloylamnino]ethyl-2'-(trimethylammonio)-ethylphosphate, 3-[(meth)acryloylamino]propyl-2'-(trimethylammonio) ethylphosphate, 4-[(meth)acryloylamino]butyl-2'-(trimethylammonio)ethylphosphate, 5-((meth)acryloyloxy)pentyl-2'-(trimethylammonio)ethyl phosphate, 6-((meth)acryloyloxy)hexyl-2'-(trimethylammonio)-ethylphosphate, 2-((meth)acryloyloxy)ethyl-2'-(triethylammonio)ethylphosphate, 2-((meth)acr-yloyloxy)ethyl-2'-(tripropylammonio)ethylphosphate, 2-((meth)acryloyloxy)ethyl-2'-(tributylammonio)ethyl phosphate, 2-((meth)acryloyloxy)propyl-2'-(trimethylammonio)-ethylphosphate, 2-((meth)acryloyloxy)butyl-2'-(trimethylammonio) ethylphosphate, 2-((meth)acryloyloxy)pentyl-2'-(trimethylammonio)ethylphosphate, 2-((meth)acryloyloxy)hexyl-2'-(trimethylammonio)ethyl phosphate, 2-(vinyloxy)ethyl-2'-(trimethylammonio)ethylphosphate, 2-(allyloxy)ethyl-2'-(trimethylammonio)ethylphosphate, 2-(vinyloxycarbonyl)ethyl-2'-(trimethylammonio)ethyl phosphate, 2-(allyloxycarbonyl)ethyl-2'-(trimethylammonio)-ethylphosphate, 2-(vinylcarbonylamino)ethyl-2'-(trimethylammonio)-ethylphosphate, 2-(allyloxycarbonylamino)ethyl-2'-(trimethylammonio)ethyl phosphate, 2-(butenoyloxy)ethyl-2'-(trimethylammonio)ethylphosphate, those described in U.S. Pat. No. 5,461,433 (herein incorporated by reference in its entirety), and combinations thereof.

More preferably, a hydrophilic polymer as a hydrophilicity-enhancing agent is PEG-$NH_2$; PEG-SH; PEG-COOH; $H_2$N-PEG-$NH_2$; HOOC-PEG-COOH; HS-PEG-SH; $H_2$N-PEG-COOH; HOOC-PEG-SH; $H_2$N-PEG-SH; multi-arm PEG with one or more amino, carboxyl or thiol groups; PEG dendrimers with one or more amino, carboxyl or thiol groups; a monoamino-, monocarboxyl-, diamino- or dicarboxyl-terminated homo- or copolymer of a non-reactive hydrophilic vinylic monomer selected from the group consisting of (meth)acryamide, N-vinylpyrrolidone (NVP), N-vinyl-N-methyl acetamide, glycerol (meth)acrylate, hydroxyethyl (meth)acrylate, N-hydroxyethyl (meth)acrylamide, N-hydroxypropyl (meth)acrylamide, $C_1$-$C_4$-alkoxy polyethylene glycol (meth)acrylate having a weight average molecular weight of up to 400 Daltons, vinyl alcohol, N-methyl-3-methylene-2-pyrrolidone, 1-methyl-5-methylene-2-pyrrolidone, 5-methyl-3-methylene-2-pyrrolidone, N,N-dimethylaminoethyl (meth)acrylate, N,N-dimethylaminopropyl (metha)crylamide, (meth)acryloyloxyethyl phosphorylcholine, and combinations thereof; a copolymer which is a polymerization product of a composition comprising (1) from about 0.1% to about 30%, preferably from about 0.5% to about 20%, more preferably from about 1% to about 15%, by weight of acrylic acid, $C_1$-$C_3$ alkylacrylic acid, allylamine and/or amino-$C_2$-$C_4$ alkyl (meth)acrylate, and (2) at least one non-reactive hydrophilic vinylic monomer selected from the group consisting of acryamide, N,N-dimethylacrylamide, N-vinylpyrrolidone, a phosphorylcholine-containing vinylic monomer, N-vinyl-N-methyl acetamide, glycerol (meth)acrylate, hydroxyethyl (meth) acrylate, N-hydroxyethyl (meth)acrylamide, $C_1$-$C_4$-alkoxy polyethylene glycol (meth)acrylate having a weight average molecular weight of up to 400 Daltons, vinyl alcohol, and combination thereof.

Most preferably, the hydrophilicity-enhancing agent as a hydrophilicity-enhancing agent is PEG-$NH_2$; PEG-SH; PEG-COOH; mono-(primary or secondary amino)-, monocarboxyl-, di-(primary or secondary amino)- or dicarboxyl-terminated polyvinylpyrrolidone; mono-(primary or secondary amino)-, monocarboxyl-, di-(primary or secondary amino)- or dicarboxyl-terminated polyacrylamide; mono-(primary or secondary amino)-, monocarboxyl-, di-(primary or secondary amino)- or dicarboxyl-terminated poly(DMA); mono-(primary or secondary amino)- or monocarboxyl-, di-(primary or secondary amino)- or dicarboxyl-terminated poly(DMA-co-NVP); mono-(primary or secondary amino)-, monocarboxyl-, di-(primary or secondary amino)- or dicarboxyl-terminated poly(NVP-co-N,N-dimethylaminoethyl (meth)acrylate)); mono-(primary or secondary amino)-, monocarboxyl-, di-(primary or secondary amino)- or dicarboxyl-terminated poly(vinylalcohol); mono-(primary or secondary amino)-, monocarboxyl-, di-(primary or secondary amino)- or dicarboxyl-terminated poly[(meth)acryloyloxyethyl phosphrylcholine] homopolymer or copolymer; mono-(primary or secondary amino)-, monocarboxyl-, di-(primary or secondary amino)- or dicarboxyl-terminated poly(NVP-co-vinyl alcohol); mono-(primary or secondary amino)-, monocarboxyl-, di-(primary or secondary amino)- or dicarboxyl-terminated poly(N,N-dimethylacrylamide-co-vinyl alcohol); poly[(meth)acrylic acid-co-acrylamide] with from about 0.1% to about 30%, preferably from about 0.5% to about 20%, more preferably from about 1% to about 15%, by weight of (meth)acrylic acid; poly[(meth)acrylic acid-co-NVP) with from about 0.1% to about 30%, preferably from about 0.5% to about 20%, more preferably from about 1% to about 15%, by weight of (meth)acrylic acid; a copolymer which is a polymerization product of a composition comprising (1) (meth)acryloyloxyethyl phosphorylcholine and (2) from about 0.1% to about 30%, preferably from about 0.5% to about 20%, more preferably from about 1% to about 15%, by weight of acrylic acid, $C_1$-$C_3$ alkylacrylic acid, allylamine and/or amino-$C_2$-$C_4$alkyl (meth)acrylate; and combination thereof.

PEGs with functional groups and multi-arm PEGs with functional groups can be obtained from various commercial suppliers, e.g., Polyscience, and Shearwater Polymers, inc., etc.

Mono-(primary or secondary amino)-, monocarboxyl-, di-(primary or secondary amino)- or dicarboxyl-terminated homo- or copolymers of one or more non-reactive hydrophilic vinylic monomers or of a phosphorylcholine-containing vinylic monomer can be prepared according to procedures described in U.S. Pat. No. 6,218,508, herein incorporated by reference in its entirety. For example, to prepare a di-(primary or secondary amino)- or dicarboxyl-terminated homo- or co-polymer of a non-reactive hydrophilic vinylic monomer, the non-reactive vinylic monomer, a chain transfer agent with a primary or secondary amino or carboxyl group (e.g., 2-aminoethanethiol, 2-mercaptopropinic acid, thioglycolic acid, thiolactic acid, or other hydroxymercaptanes, aminomercaptans, or carboxyl-containing mercaptanes) and optionally other vinylic monomer are copolymerized (thermally or actinically) with a reactive vinylic monomer (having a primary or secondary amino or carboxyl group), in the presence of an free-radical initiator. Generally, the molar ratio of chain transfer agent to that of all of vinylic monomers other than the reactive vinylic monomer is from about 1:5 to about 1:100, whereas the molar ratio of chain transfer agent to the reactive vinylic monomer is 1:1. In such preparation, the chain transfer agent with primary or secondary amino or carboxyl group is used to control the molecular weight of the resultant hydrophilic polymer and forms a terminal end of the resultant hydrophilic polymer so as to provide the resultant hydrophilic polymer with one terminal primary or secondary amino or carboxyl group, while the reactive vinylic monomer provides the other terminal carboxyl or primary or secondary amino group to the resultant hydrophilic polymer. Similarly, to prepare a mono-(primary or secondary amino)- or mono-carboxyl-terminated homo- or co-polymer of a non-reactive hydrophilic vinylic monomer, the non-reactive vinylic monomer, a chain transfer agent with a primary or secondary amino or carboxyl group (e.g., 2-aminoethanethiol, 2-mercaptopropinic acid, thioglycolic acid, thiolactic acid, or other hydroxymercaptanes, aminomercaptans, or carboxyl-containing mercaptanes) and optionally other vinylic monomers are copolymerized (thermally or actinically) in the absence of any reactive vinylic monomer.

Copolymers comprising a non-reactive hydrophilic vinylic monomer and a reactive vinylic monomer (e.g., a carboxyl-containing vinylic monomer, a primary amino group-containing vinylic monomer or a secondary amino group-containing vinylic monomer) can be prepared according to any well-known radical polymerization methods or obtained from commercial suppliers. Copolymers containing methacryloyloxyethyl phosphorylcholine and carboxyl-containing vinylic monomer (or amino-containing vinylic monomer) can be obtained from NOF Corporation (e.g., LIPIDURE®-A and -AF).

The weight average molecular weight $M_w$ of the hydrophilic polymer having at least one amino, carboxyl or thiol group (as a hydrophilicity-enhancing agent) is preferably from about 500 to about 5,000,000, more preferably from about 1,000 to about 2,000,000, even more preferably from about 5,000 to about 1,000,000 Daltons.

In accordance with the invention, the reactive mixture either has a pH of at least 8.0 (preferably at least 8.5, more preferably at least 9.0, even more preferably at least 9.5), or comprises one or more non-polymeric ionic compounds present in a total amount of from about 85 millimolars (mM) to about 135 mM (preferably about 90 mM to about 130 mM, more preferably from about 100 mM to about 120 mM) or both thereof.

A person skilled in the art understands well how to adjust the pH of the reactive mixture, e.g., by adding a base (e.g., NaOH, KOH, $NH_4OH$, or mixture thereof) or an acid (e.g., HCl, $H_2SO_4$, $H_3PO_4$, citric acid, acetic acid, boric acid, or mixture thereof).

In accordance with the invention, any non-polymeric ionic compounds can be used in the reactive mixture. Preferably, non-polymeric ionic compounds are those used as ionic tonicity-adjusting agents and ionic buffering agents used in an ophthalmic solutions. Examples of preferred ionic tonicity-adjusting agents includes without limitation sodium chloride, potassium chloride, and combinations thereof. Examples of preferred ionic buffering agents includes various salts of phosphoric acid (e.g. $NaH_2PO_4$, $Na_2HPO_4$, $Na_3PO_4$, $KH_2PO_4$, $K_2HPO_4$, $K_3PO_4$, or mixtures thereof), various salts of boric acid (e.g., sodium borate, potassium borate, or mixture thereof), various salts of citric acid (e.g., monosodium citrate, disodium citrate, trisodium citrate, monopotassium citrate, dipotassium citrate, tripotassium citrate, or mixtures thereof), various salts of carbonic acid (e.g., $Na_2CO_3$, $NaHCO_3$, $K_2CO_3$, $KHCO_3$, or mixture thereof).

The reactive mixture can be prepared by dissolving a desired amount of an azetidinium-containing polymer, a desired amount of a hydrophilicity-enhancing agent with at least one reactive functional group, and desired amounts of other components (e.g., ionic buffering agents, ionic tonicity-adjusting agents, etc.) in water (or a mixture of water and a minority amount of a water-soluble organic solvent) to form an aqueous solution and then adjusting the pH of the aqueous solution if necessary.

In accordance with the invention, the reaction between a hydrophilicity-enhancing agent and an azetidinium-containing polymer is carried out at a temperature of about 35° C. to about 85° C. for a period of time sufficient (about 6 hours or less, preferably about 5 hours, more preferably from about 2 hour to about 4 hours) to obtain the water-soluble thermally-crosslinkable polymeric material which comprises azetidinium groups and in which the hydrophilicity-enhancing agent is covalently attached to the azetidinium-containing polymer through one or more covalent linkages each formed between one azetidinium group and one reactive functional group. It should be understood that the reaction time should be long enough to covalently attach the hydrophilicity-enhancing agent onto the polymer chain of the azetidinium-containing polymer, but should be short enough not to consume all the azetidinium groups of the azetidinium-containing polymer and not to form a gel (i.e., not water-soluble) due to the too many crosslinkages formed between the azetidinium-containing polymer and the hydrophilicity-enhancing agent. A resultant polymeric material is a lightly-crosslinked polymeric material which has a highly-branched structure and still comprises thermally-crosslinkable azetidinium groups.

In accordance with the invention, the concentration ratio of a hydrophilicity-enhancing agent relative to an azetidinium-containing polymer must be selected not to render a resultant water-soluble thermally-crosslinkable polymeric material water-insoluble (i.e., a solubility of less than 0.005 g per 100 ml of water at room temperature) and not to consume more than about 99%, preferably about 98%, more preferably about 97%, even more preferably about 96% of the azetidinium groups of the azetidinium-containing polymer.

In a preferred embodiment, the reactive mixture comprises from 0.01% to about 10% by dry weight (preferably from 0.05% to about 5% by weight, more preferably from 0.08% to about 1% by weight, even more preferably from 0.1% to about 0.4% by weight) of an azetidinium-containing polymer and from about 0.01% to about 10% by weight (preferably from 0.02% to about 5% by weight, more preferably from 0.05% to about 2% by weight, even more preferably from 0.08% to about 1.0% by weight) of a hydrophilicity-enhancing agent having at least one reactive function group (carboxyl, primary amino, secondary amino group), the concentration ratio (dry weight base) of the azetidinium-containing polymer to the hydrophilicity-enhancing agent is from about 1000:1 to 1:1000 (preferably from about 500:1 to about 1:500, more preferably from about 250:1 to about 1:250, even more preferably from about 100:1 to about 1:100).

An azetidinium-containing vinylic monomer of the invention can find particular use in preparing copolymers suitable for forming non-silicone hydrogel coatings on SiHy contact lenses.

A water-soluble thermally-crosslinkable polymeric material produced according to a method of the invention can find particular use in preparing a packaging solution used for packaging and autoclaving medical devices, especially contact lenses. Such a packaging solution is especially suitable for forming a relatively-thick and soft non-silicone hydrogel coatings on hydrogel contact lenses or medical devices according to the in-package-crosslinking (IPC) processes described in U.S. Pat. No. 8,529,057 (herein incorporated by reference in its entirety). The resultant non-silicone hydrogel coatings can have a superior lubricity (a friction rating of 0) with minimized or no surface cracking.

Lens packages (or containers) are well known to a person skilled in the art for autoclaving and storing a soft contact lens. Any lens packages can be used in the invention. Preferably, a lens package is a blister package which comprises a base and a cover, wherein the cover is detachably sealed to the base, wherein the base includes a cavity for receiving a sterile packaging solution and the contact lens.

Lenses are packaged in individual packages, sealed, and autoclaved (a sterilization procedure involving heating the packaging of a contact lens to a temperature of from about 118° C. to about 125° C. for approximately 20-40 minutes under pressure) prior to dispensing to users. A person skilled in the art will understand well how to seal and autoclave lens packages.

In accordance with the invention, a packaging solution contains at least one buffering agent and one or more other ingredients known to a person skilled in the art. Examples of other ingredients include without limitation, tonicity agents, surfactants, antibacterial agents, preservatives, and lubricants (e.g., polyethylene glycol, cellulose derivatives, polyvinyl alcohol, polyvinylpyrrolidone).

The packaging solution contains a buffering agent in an amount sufficient to maintain a pH of the packaging solution in the desired range, for example, preferably in a physiologically acceptable range of 6.5 to 7.5. Any known, physiologically compatible buffering agents can be used. Suitable buffering agents as a constituent of the contact lens care composition according to the invention are known to the person skilled in the art. Examples are borate buffers, citrate buffers, bicarbonate buffers, phosphate buffers, TRIS (2-amino-2-hydroxymethyl-1,3-propanediol), Bis-Tris [i.e., Bis-(2-hydroxyethyl)-imino-tris-(hydroxymethyl)-methane], Bis-Tris propane [i.e., 1,3-bis(tris(hydroxymethyl) methylamino)propane], bis-aminopolyols, triethanolamine, ACES (N-(2-hydroxyethyl)-2-aminoethanesulfonic acid), BES (N,N-Bis(2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS (3-[N-morpholino]-propanesulfonic acid), PIPES (piperazine-N,N'-bis(2-ethanesulfonic acid), TES (N-[Tris (hydroxymethyl)methyl]-2-aminoethanesulfonic acid), salts thereof. The amount of each buffer agent in a packaging solution is preferably from 0.01% to 0.8%; most preferably from about 0.02% to about 0.4% by weight.

The packaging solution has a tonicity of from about 200 to about 450 milliosmol (mOsm), preferably from about 250 to about 350 mOsm. The tonicity of a packaging solution can be adjusted by adding organic or inorganic substances which affect the tonicity. Suitable occularly acceptable tonicity agents include, but are not limited to sodium chloride, potassium chloride, glycerol, propylene glycol, polyols, mannitols, sorbitol, xylitol and mixtures thereof.

A packaging solution of the invention has a viscosity of from about 1 centipoise to about 5 centipoises, at 25° C.

The packaging solution comprises preferably from about 0.01% to about 2%, more preferably from about 0.05% to about 1.5%, even more preferably from about 0.1% to about 1%, most preferably from about 0.2% to about 0.5%, by weight of a water-soluble thermally-crosslinkable hydrophilic polymeric material of the invention.

In accordance with the invention, during autoclave, a water-soluble thermally-crosslinkable polymeric material can be crosslinked effectively with the functional groups (e.g., primary or secondary amino groups, thiol groups, and/or carboxylic acid groups) on and/or near the surface of a hydrogel contact lens to form a crosslinked hydrogel coating which are wettable and ophthalmically compatible, while those azetidinium groups which do not participate in crosslinking reaction may be hydrolyzed into 2,3-dihydroxypropyl (HO—$CH_2$—CH(OH)—$CH_2$—) groups. After autoclave, the water-soluble thermally-crosslinkable polymeric material present in the lens packaging solution, if applicable, would have been converted to a non-reactive polymeric wetting agent capable of improving a lens's insert comfort.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together, as illustrated below:

1. A method for producing a water-soluble thermally-crosslinkable polymeric material, comprising the steps of:
   (1) obtaining a reactive mixture which is an aqueous solution comprising
      (a) an azetidinium-containing polymer having azetidinium groups,
      (b) a hydrophilicity-enhancing agent (i.e., a wetting agent) having at least one reactive functional group selected from the group consisting of primary amino group, secondary amino group, carboxyl group, thiol group, and a combination thereof, and (c) one or more non-polymeric ionic compounds, provided that the aqueous solution either has a pH of at least 8.0 and/or that the non-polymeric ionic compounds are present in the aqueous solution in a total amount of (i) 0 mM to about 135 mM if the hydrophilicity-enhancing agent is non-ionic or positively-charged at the pH of the aqueous solution or (ii) from about 20 millimolars (mM) to about 135 mM if the hydrophilicity-enhancing agent is negatively-charged charged at the pH of the aqueous solution; and (2) heating the reactive mixture to reach a reaction temperature of from about 40° C. to about 85° C. and maintaining the temperature of the reactive mixture at the reaction temperature for a time period to obtain the water-soluble thermally-crosslinkable polymeric material in which the hydrophilicity-enhancing agent is covalently attached to the azetidinium-containing polymer through one or more covalent linkages each formed between one azetidinium group and one reactive functional group, wherein the water-soluble thermally-crosslinkable polymeric material comprises azetidinium groups.

2. The method of invention 1, wherein the aqueous solution either has a pH of at least 8.0.

3. The method of invention 1, wherein the aqueous solution either has a pH of at least 8.5.

4. The method of invention 1, wherein the aqueous solution either has a pH of at least 9.0.

5. The method of invention 1, wherein the aqueous solution either has a pH of at least 9.5.

6. The method of any one of inventions 1 to 5, wherein the non-polymeric ionic compounds are present in the aqueous solution in a total amount of (i) from about 0.5 mM to about 130 mM if the hydrophilicity-enhancing agent is non-ionic or positively-charged at the pH of the aqueous solution or (ii) from about 25 mM to about 130 mM if the hydrophilicity-enhancing agent is negatively-charged at the pH of the aqueous solution.

7. The method of any one of inventions 1 to 5, wherein the non-polymeric ionic compounds are present in the aqueous solution in a total amount of (i) from about 1 mM to about 120 mM if the hydrophilicity-enhancing agent is non-ionic or positively-charged at the pH of the aqueous solution or (ii) from about 30 mM to about 120 mM if the hydrophilicity-enhancing agent is negatively-charged at the pH of the aqueous solution.

8. The method of any one of inventions 1 to 7, wherein the reactive mixture comprises from 0.01% to about 10% by weight of the azetidinium-containing polymer and from about 0.01% to about 10% by weight of the hydrophilicity-enhancing agent having at least one reactive function group, provided that the concentration ratio of the azetidinium-containing polymer to the hydrophilicity-enhancing agent in the reactive mixture is from about 1000:1 to 1:1000.

9. The method of any one of inventions 1 to 8, wherein the reactive mixture comprises from 0.05% to about 5% by weight of the azetidinium-containing polymer.

10. The method of any one of inventions 1 to 8, wherein the reactive mixture comprises from 0.08% to about 1% by weight of the azetidinium-containing polymer.

11. The method of any one of inventions 1 to 8, wherein the reactive mixture comprises from 0.1% to about 0.4% by weight of the azetidinium-containing polymer.

12. The method of any one of inventions 1 to 11, wherein the reactive mixture comprises from about 0.02% to about 5% by weight of the hydrophilicity-enhancing agent having at least one reactive function group.

13. The method of any one of inventions 1 to 11, wherein the reactive mixture comprises from 0.05% to about 2% by weight of the hydrophilicity-enhancing agent having at least one reactive function group.

14. The method of any one of inventions 1 to 11, wherein the reactive mixture comprises from 0.08% to about 1.0% by weight of the hydrophilicity-enhancing agent having at least one reactive function group.

15. The method of any one of inventions 1 to 14, wherein the concentration ratio of the azetidinium-containing polymer to the hydrophilicity-enhancing agent in the reactive mixture is from about 500:1 to about 1:500.

16. The method of any one of inventions 1 to 14, wherein the concentration ratio of the azetidinium-containing polymer to the hydrophilicity-enhancing agent in the reactive mixture is from about 250:1 to about 1:250.

17. The method of any one of inventions 1 to 14, wherein the concentration ratio of the azetidinium-containing polymer to the hydrophilicity-enhancing agent in the reactive mixture is from about 100:1 to about 1:100.

18. The method of any one of inventions 1 to 17, wherein the azetidinium-containing polymer is an epichlorohydrin-functionalized polyamine.

19. The method of invention 18, wherein the epichlorohydrin-functionalized polyamine is polyamidoamine-epichlorohydrin.

20. The method of invention 18, wherein the epichlorohydrin-functionalized polyamine is a poly(2-oxazoline-co-ethyleneimine)-epichlorohydrin.

21. The method of any one of inventions 1 to 17, wherein the azetidinium-containing polymer is a homopolymer or copolymer of an azetidinium-containing vinylic monomer.

22. The method of any one of inventions 1 to 21, wherein the hydrophilicity-enhancing agent is: a polyethylene glycol having one sole primary or secondary amino, carboxyl or thiol group; a polyethylene glycol with two terminal primary or secondary amino, carboxyl and/or thiol groups; a multi-arm polyethylene glycol with one or more primary or secondary amino, carboxyl and/or thiol groups; a polyethylene glycol dendrimer with one or more primary or secondary amino, carboxyl and/or thiol groups.

23. The method of any one of inventions 1 to 21, wherein the hydrophilicity-enhancing agent is a copolymer which is a polymerization product of a composition comprising (1) about 60% or less by weight of one or more reactive vinylic monomers and (2) one or more non-reactive hydrophilic vinylic monomers.

24. The method of invention 23, wherein said one or more reactive vinylic monomers are vinylic monomers having a carboxyl group.

25. The method of invention 24, wherein said one or more reactive vinylic monomers are selected from the group consisting of acrylic acid, $C_1$-$C_4$ alkylacrylic acid (e.g., methacrylic ethylacrylic acid, propylacrylic acid, butylacrylic acid), N-2-(meth)acrylamidoglycolic acid, beta methyl-acrylic acid (crotonic acid), alpha-phenyl acrylic acid, beta-acryloxy propionic acid, sorbic acid, angelic acid, cinnamic acid, 1-carobxy-4-phenyl butadiene-1,3, itaconic acid, citraconic acid, mesaconic acid, glutaconic acid, aconitic acid, maleic acid, fumaric acid, tricarboxy ethylene, and combinations thereof.

26. The method of invention 24, wherein said one or more reactive vinylic monomers are acrylic acid, methylacrylic acid, or combinations thereof.

27. The method of invention 23, wherein said one or more reactive vinylic monomers are vinylic monomers having a primary or secondary amino group.

28. The method of invention 27, wherein said one or more reactive vinylic monomers are amino-$C_2$-$C_6$ alkyl (meth)acrylate, $C_1$-$C_6$ alkylamino-$C_2$-$C_6$ alkyl (meth)acrylate, allylamine, vinylamine, amino-$C_2$-$C_6$ alkyl (meth)acrylamide, $C_1$-$C_6$ alkylamino-$C_2$-$C_6$ alkyl (meth)acrylamide, and combinations thereof.

29. The method of any one of inventions 23 to 28, wherein said one or more non-reactive vinylic monomers are selected from the group consisting of (meth)acrylamide, N,N-dimethyl (meth)acrylamide, N-vinylpyrrolidone (NVP), N-vinyl formamide, N-vinyl acetamide, N-vinyl isopropylamide, N-vinyl-N-methyl acetamide, N,N-dimethylaminoethyl (meth)acrylate, N,N-dimethylaminopropyl (meth)acrylamide, glycerol (meth)acrylate, 3-(meth)acryloylamino-1-propanol, N-hydroxyethyl (meth)acrylamide, N-hydroxypropyl (meth)acrylamide, N-[tris(hydroxymethyl)methyl]-acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 2-hydroxyethyl (meth)acrylate, hydroxypropyl (meth)acrylate, $C_1$-$C_4$-alkoxy polyethylene glycol (meth)acrylate having a weight average molecular weight of up to 1500 Daltons, allyl alcohol, vinyl alcohol, and combinations thereof.

30. The method of any one of inventions 23 to 28, wherein said one or more non-reactive vinylic monomers are selected from the group consisting of acryamide, N,N-dimethylacrylamide, N-vinylpyrrolidone, N-vinyl-N-methyl acetamide, glycerol (meth)acrylate, hydroxyethyl (meth)acrylate, N-hydroxyethyl (meth)acrylamide, $C_1$-$C_4$-alkoxy polyethylene glycol (meth)acrylate having a weight average molecular weight of up to 400 Daltons, vinyl alcohol, and combination thereof.

31. The method of any one of inventions 23 to 28, wherein said one or more non-reactive vinylic monomers are phosphorylcholine-containing vinylic monomers.

32. The method of any one of inventions 23 to 28, wherein said one or more non-reactive vinylic monomers are methacryloyloxyethyl phosphorylcholine.

33. The method of any one of inventions 23 to 32, wherein the composition comprises about 50% or less by weight of said one or more reactive vinylic monomers.

34. The method of any one of inventions 23 to 32, wherein the composition comprises from about 0.1% to about 30% by weight of said one or more reactive vinylic monomers.

35. The method of any one of inventions 23 to 32, wherein the composition comprises from about 0.5% to about 20% by weight of said one or more reactive vinylic monomers.

36. The method of any one of inventions 23 to 32, wherein the composition comprises from about 1% to about 15% by weight of said one or more reactive vinylic monomers.

37. The method of any one of inventions 1 to 21, wherein the hydrophilicity-enhancing agent is a primary or secondary amino- or carboxyl-containing polysaccharide, hyaluronic acid, chondroitin sulfate, and combinations thereof.

38. The method of any one of inventions 1 to 21, wherein the hydrophilicity-enhancing agent is a primary or secondary amino-containing monosaccharide, a carboxyl-containing monosaccharide, a thiol-containing monosaccharide, a primary or secondary amino-containing disaccharide, a carboxyl-containing disaccharide, a thiol-containing disaccharide, a primary or secondary amino-containing oligosaccharide, a carboxyl-containing oligosaccharide, a thiol-containing oligosaccharide, or a combination thereof.

39. The method of any one of inventions 1 to 38, wherein the concentrations of the hydrophilicity-enhancing agent and the azetidinium-containing polymer in the aqueous solution are at least about 10 times of a targeted concentration of the water-soluble thermal-crosslinkable polymeric material in a packaging solution to be used for forming a non-silicone hydrogel coating on a hydrogel contact lens or a medical device according to in-package-crosslinking (IPC) process.

40. A process for preparing an in-package-crosslinking saline, comprising:

obtaining a water-soluble thermally-crosslinkable polymeric material according to a method of any one of inventions 1 to 39;

adding and dissolving targeted amounts of the water-soluble thermally-crosslinkable polymeric material, of one more buffering agents, and of one or more tonicity agents in water to form a solution;

and adjusting the pH of the solution to form the in-package-crosslinking solution which has a pH of from about 6.5 to about 7.5, a tonicity of from about 200 to about 450 milliosmol (mOsm), and a viscosity of from about 1 centipoise to about 5 centipoises at 25° C.

The previous disclosure will enable one having ordinary skill in the art to practice the invention. Various modifications, variations, and combinations can be made to the various embodiment described herein. In order to better enable the reader to understand specific embodiments and the advantages thereof, reference to the following examples is suggested. It is intended that the specification and examples be considered as exemplary.

The following abbreviations are used in the following examples: MCR-M07 represents monobutyl-terminated monomethacryloxypropyl-terminated polydimethylsiloxane (M.W. 600 to 800 g/mol from Gelest); NVP represents N-vinylpyrrolidone; MMA represents methyl methacrylate; TEGDMA represent triethyleneglycol dimethacrylate; EGDMA represents ethylene glycol methyl ether methacrylate; AMA represents allyl methacrylate; VAZO 64 represents 2,2'-dimethyl-2,2'azodipropiononitrile; Nobloc is 2-[3-(2H-Benzotriazol-2-yl)-4-hydroxyphenyl]ethyl methacrylate from Aldrich; RB246 is Reactive Blue 246 from Arran; LM-CEPDMS represents a di-methacrylate-terminated chain-extended polydimethylsiloxane (M.W. 6000 g/mol) which has three polydimethylsiloxane (PDMS) segments linked via diurethane linkages between two PDMS segments and is prepared according to method similar to what described in Example 2 of U.S. Pat. No. 8,529,057 (herein incorporated by reference in its entirety); X22-1661A represents a di-methacrylate-terminated polysiloxane (M.W. 9K g/mol) of the following structural formula

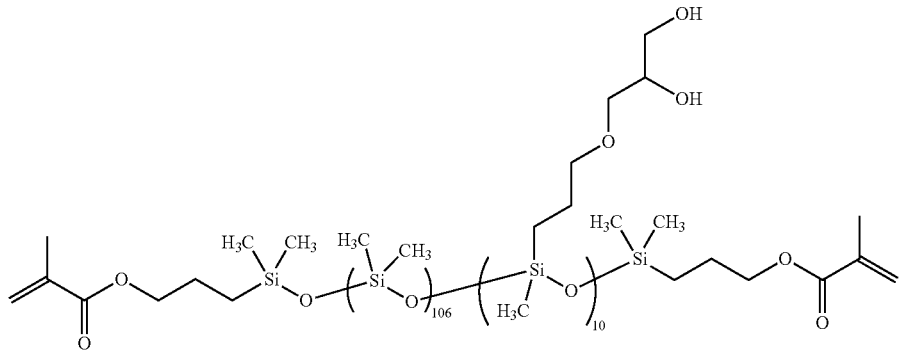

Example 1

Manually Rubbing Tests.

The lenses are manually rubbed according to product insert with RENU® multi-purpose lens care solution (or another multi-purpose lens care solution) for 20 seconds and placed back to the lens case containing fresh lens care solution. The above procedure is repeated for a given times, e.g., from 1 to 30 times, (i.e., number of repetitions of manually rubbing tests which imitate cleaning and soaking cycles). It is stated in the examples throughout this disclosure such as 14× cycled which means manually rubbed 14 times.

Lubricity Evaluation.

The lubricity of a lens is evaluated by using a finger-felt lubricity test which characterizes qualitatively the slipperiness of a lens surface on a friction rating scale of from 0 to 4. The higher the friction rating is, the lower the slipperiness (or lubricity).

Commercial lenses: DAILIES® TOTAL1®; ACUVUE® OASYS™; ACUVUE® ADVANCE PLUS™; DAILIES® Aqua Comfort Plus®; and AIR OPTIX®, are assigned a friction rating (designated "FR" hereinafter) of 0, 1, 2, 3, and 4 respectively. They are used as standard lenses for determining the friction rating of a lens under test.

The samples are placed in PBS for at least two rinses of 30 minutes each and then transferred to fresh PBS before the evaluation. Before the evaluation, hands are rinsed with a soap solution, extensively rinsed with DI water and then dried with KimWipe® towels. The samples are handled between the fingers and a numerical number is assigned for each sample relative to the above standard lenses described above. For example, if lenses are determined to be only slightly better than AIR OPTIX® lenses, then they are assigned a number 3. The value of a friction rating is one obtained by averaging the results of at least two friction ratings of a contact lens by two or more persons and/or by averaging the friction ratings of two or more contact lenses (from the identical batch of lens production) by one person.

Surface Wettability Tests.

Water contact angle (WCA) on a contact lens is a general measure of the surface wettability of a contact lens. In particular, a low water contact angle corresponds to more wettable surface. Average contact angles (Sessile Drop) of contact lenses are measured using a VCA 2500 XE contact angle measurement device from AST, Inc., located in Boston, Mass. This equipment is capable of measuring advancing contact angles ($\theta_a$) or receding contact angles ($\theta_r$) or sessile (static) contact angles. Unless specified, water contact angle is sessile (static) contact angle. The measurements are performed on fully hydrated contact lenses and immediately after blot-drying as follows. A contact lens is removed from the vial and washed 3 times in ~200 ml of fresh DI water in order to remove loosely bound packaging additives from the lens surface. The lens is then placed on top of a lint-free clean cloth (Alpha Wipe TX1009), dabbed well to remove surface water, mounted on the contact angle measurement pedestal, blown dry with a blast of dry air and finally the sessile drop contact angle is automatically measured using the software provided by the manufacturer. The DI water used for measuring the contact angle has a resistivity >18MΩcm and the droplet volume used is 2 μl. Typically, uncoated silicone hydrogel lenses (after autoclave) have a sessile drop contact angle around 120 degrees. The tweezers and the pedestal are washed well with Isopropanol and rinsed with DI water before coming in contact with the contact lenses.

Water Break-Up Time (WBUT) Tests.

The surface hydrophilicity of lenses (after autoclave) is assessed by determining the time required for the water film to start breaking on the lens surface. Briefly, lenses are removed from the vial and placed in PBS (phosphate buffered saline) for at least two rinses of 30 minutes each and then transferred to fresh PBS in order to remove loosely bound packaging additives from the lens surface. The lens is removed from the solution and held against a bright light source. The time that is needed for the water film to break (de-wet) exposing the underlying lens material is noted visually. Uncoated lenses typically instantly break upon removal from PBS and are assigned a WBUT of 0 seconds. Lenses exhibiting WBUT ≥10 seconds are considered to have a hydrophilic surface and are expected to exhibit adequate wettability (ability to support the tear film) on-eye.

Surface Cracking (SC) Tests-Method 1

Method 1 for evaluating surface cracking is carried out as follows. Remove lens from the package. Invert the lens inside-out gently (i.e., rendering the lens in the invert form) by holding the edge of the lens between the thumb and index finger of one hand. The concave side of the lens should face the experimenter's body. With the thumb and/or index finger of the other hand, gently bend the top of the lens over the index finger holding the lens until the lens confirmation inverts. Following that, fold the lens gently in half and apply slight pressure to the folded lens. Afterward, revert the lens to its original form prior to the lens inversion and repeat the aforementioned steps. Place the lens in a Petri dish and inspect lens using a darkfield stereomicroscope. Lens surface cracking is first inspected at low magnification (i.e., 10-20×) with focus on the center of the lens, if crack lines are not distinguishable, lens is further inspected at high magnification (e.g., 35-45×). If no cracking is observed in 45× magnifications, lens receives a surface cracking rating of zero (0). If cracking is observed, the cracking rating is accomplished by counting the number of split lines: rating of 1=2-4 lines in field-of-view; rating of 2=5-8 lines; rating of 3≥8 lines.

Surface Cracking (SC) Tests-Method 2

Method 2 for evaluating surface cracking is composed of two parts in lens handling: Part I is rubbing; and Part II is 2 s cycling with unused saline. Part I is conducted as follow: (1) remove lens from package; (2) rub lens across finger; (3) rinse lens with fresh saline; (4) submerge lens with unused saline for inspection using a stereomicroscope. Rate sample based on description from method 1. After rubbing test is completed, proceed to Part II as describe: (1) cycle lens for 2 seconds on both surface with saline; (2) rinse lens with unused saline; (3) submerge lens with unused saline for submerged lens with unused saline for inspection using a stereomicroscope.

Example 2

Preparation of Polymerizable Compositions

Two lens formulations (polymerizable compositions), I and II, are prepared to have compositions (in unit parts) as shown in Table 1.

TABLE 1

| Formulation No. | | Compositions (Unit parts) | |
|---|---|---|---|
| | | I | II |
| Monomethacryloxypropyl terminated polydimethylsiloxane, asymmetric (MW 600-800) | MCR-M07 | 34 | 34 |
| Low Molecular weight Chain extended polydimethylsiloxane | LM-CEPDMS | 6 | 0 |
| Glycerol polydimethylsiloxane | X22-1661A | 0 | 6 |
| 1-Vinyl-2-pyrrolidinone | NVP | 40 | 40 |
| Methyl methacrylate | MMA | 10 | 10 |
| Ethylene glycol methyl ether methacrylate | EGMA | 10 | 10 |
| Triethylene glycol dimethacrylate | TEGDMA | 0.2 | 0.4 |
| Allyl methaylate | AMA | 0.1 | 0.1 |
| 2-[3-(2H-Benzotriazol-2-yl)-4-hydroxyphenyl]ethyl methacrylate | Nobloc | 0.9 | 1.0 |
| 2,2'-dimethyl-2,2'azodipropiononitrile | Vazo 64 | 0.5 | 0.5 |
| Reactive Blue 246 | RB 246 | 0.01 | 0 |
| Reactive Blue 247 | RB 247 | 0 | 0.01 |
| Tert-amyl alcohol | t-amyl-OH | 0 | 1 |

The formulations are prepared by adding listed components in their targeted amounts into a clean bottle, with a stir bar to mix at 600 rpm for 30 min at room temperature. After all the solid is dissolved, a filtration of the formulation is carried out by using 2.7 um GMF filter.

Preparation of Silicone Hydrogel Contact Lenses

A lens formulation is purged with nitrogen at room temperature for 30 to 35 minutes. The $N_2$-purged lens formulation is introduced into polypropylene molds and thermally cured under the following curing conditions: ramp from room temperature to 55° C. at a ramp rate of about 7° C./minute; holding at 55° C. for about 30 minutes; ramp from 55° C. to 80° C. at a ramp rate of about 7° C./minute; holding at 55° C. for about 30 minutes; ramp from 80° C. to 100° C. at a ramp rate of about 7° C./minute; and holding at 100° C. for about 30 minutes. The molds are opened and the molded lenses are removed from the molds.

Formulations I and II are used for coating studies in the examples below. In general, Formulation II is used unless otherwise specified.

PAA-Dip Coating of Lenses

After demolding, dry silicone hydrogel contact lenses are placed in adequate trays. Then the trays with lenses are immersed in an aqueous solution of polyacrylic acid (PAA) (ca. 0.1% by weight) for a certain periods of time, either for 120 min in one bath of PAA, or in two consecutive baths of PAA with 30 min dip in the $1^{st}$ bath and 90 min dip in the $2^{nd}$ bath. The PAA solution is prepared by dissolving an adequate amount of PAA (Mw 450K Daltons) in water (distilled or deionized water) and by adding an adequate amount of formic acid to adjust the solution pH to about 2. The PAA dip solution is heated to above room temperature, for example 40° C. Adequate agitation (e.g. horizontal shaking or up-down movement) may be used to ensure appropriate flow of PAA solution during the dip step. After PAA dip coating, the lenses are transferred to a bath with phosphate buffer (PB) for 15 min to about an hour, usually at room temperature. The PB is prepared by dissolving $NaH_2PO_4 \cdot H_2O$ and $Na_2HPO_4 \cdot 2H_2O$ in a given volume of purified water (distilled or deionized) to have about 0.044 w/w % $NaH_2PO_4 \cdot H_2O$, about 0.388 w/w/% $Na_2HPO_4 \cdot 2H_2O$. Adequate agitation (e.g. horizontal shaking or up-down movement) may be used to ensure appropriate flow of PB during the dip step. Then lenses are transferred to a bath with water for about 5~10 min, usually at room temperature. Adequate agitation (e.g. horizontal shaking or up-down movement) may be used to ensure appropriate flow of water during the dip step.

Example 3

Preparation of Water-Soluble Thermally-Crosslinkable Materials

A water-soluble thermally-crosslinkable polymeric material (i.e., "in-package-crosslinking agent) or "IPC agent") is prepared from polyamidoamine-epichlorohydrin (PAE) and poly(acrylamide-co-acrylic acid)(90/10) (i.e., poly(AAm-co-AA) 90/10 as follows. PAE solutions of different solid contents (Kymene) are purchased from Ashland as an aqueous solution and used as received. Poly(AAm-co-AA)(90/10) partial sodium salt, poly(AAm-co-AA) 90/10, Mw 200,000) is purchased from Polysciences, Inc. and used as received. The following components: 0.12 w/w % PAE, 0.13 w/w % poly(AAm-co-AA)(90/10), about 0.044 w/w % (i.e., 3.2 mM) $NaH_2PO_4$—$H_2O$, about 0.388 w/w/% (i.e., 12.9 mM) $Na_2HPO_4 \cdot 2H_2O$, and a concentration of NaCl specified in Table 1 are dissolved in a target amount of purified water (distilled or deionized water) and then pH-adjusted by adding 1 N NaOH to desired pH (e.g., 7.4). The prepared solution is placed in a container immersed in a water bath. The reaction is carried out at about 65° C. for about 6 hours. Remove the container with the solution therein from the water bath and cool it down by putting it in room temperature water, obtained an aqueous solution including a water-soluble thermally-crosslinkable polymeric material.

In-Package-Crosslinking (IPC) Saline

IPC saline is prepared from the aqueous solution prepared above that includes the formed water-soluble thermally-crosslinkable polymeric material by adding NaCl to have a concentration of about 0.79 w/w %. The pH of IPC saline is adjusted to about 7.4 by adding either 1N NaOH or 1N HCl if necessary. 5 ppm hydrogen peroxide may be added to the final IPC saline to prevent bioburden growth and the IPC saline is filtered using a 0.22 micron membrane filter.

SiHy Lenses with Hydrogel Top Coating

PAA-coated SiHy lenses obtained in Example 2 are placed in polypropylene lens packaging shells (or blisters) (one lens per shell) with 0.65 mL of the IPC saline (half of the saline is added prior to inserting the lens). The blisters are then sealed with foil and autoclaved for about 45 minutes at about 121° C., forming SiHy contact lenses with hydrogel top coatings (PAA-x-hydrophilic polymeric material) thereon.

The friction rating of resultant SiHy lenses are evaluated according to the procedures described in Example 1; and the surface cracking of the resultant SiHy lenses are determined according to SC Method 1 described in Example 1. The results are reported in Table 1.

TABLE 1

| IPC agent Preparation | | | Friction | Surface |
|---|---|---|---|---|
| [NaCl] mM | Rxn T (° C.) | Rxn t (hrs) | Rating | Cracking |
| 68 | 65 | 6 | 0, 0, 0 | 3, 3, 3 |
| 88 | 65 | 6 | 0, 0, 0 | 1, 1, 1, |
| 108 | 65 | 6 | 0, 0, 0 | 3, 3, 3 |

* [PAE] = 0.12 w/w %; [poly(AAm-co-AA)] = 0.13 w/w %; [NaH$_2$PO$_4$] = 3.2 mM; [Na$_2$HPO$_4$] = 12.9 mM.

It shows that the IPC agent prepared in a solution containing 88 mM NaCl can provide the superior lubricity (a friction rating of 0) and a minimum cracking.

Example 4

Effects of the total concentration of non-polymeric ionic compounds upon the reaction between PAE and poly(AAm-co-AA) by varying NaCl concentration while keeping phosphates concentrations (about 3.2 mM NaH$_2$PO$_4$, about 12.9 mM Na$_2$HPO$_4$) in the aqueous reaction solution, as shown in Table 2., experiments summarized in Table 2 was executed. The aqueous reaction solution without NaCl are all gelled in shorter reaction time than the one with 135 mM NaCl (i.e., about 0.79 w/w %). This indicates that the reaction between PAE and poly(AAm-co-AA) is much faster without the presence of NACl.

TABLE 2

| [PAE] (wt %) | [poly(AAm-co-AA)] (wt %) | [NaCl] (mM) | Rxn T (° C.) | Rxn t (hrs) | Results |
|---|---|---|---|---|---|
| 0.088 | 0.07 | 135 | 60 | 6 | Not gelled |
| 0.088 | 0.07 | 0 | 65 | 3 | Gelled |
| 0.088 | 0.07 | 0 | 65 | 4 | Gelled |
| 0.088 | 0.07 | 0 | 65 | 5 | Gelled |
| 0.088 | 0.0467 | 0 | 65 | 4 | Gelled |
| 0.088 | 0.0933 | 0 | 65 | 4 | Gelled |

* [NaH$_2$PO$_4$] = 3.2 mM; [Na$_2$HPO$_4$] = 12.9 mM.

Example 5

Preparation of Water-Soluble Thermally-Crosslinkable Materials

Various IPC agents are prepared according to procedures described in Example 3 with the reaction conditions shown in Table 3 and Table 4 to study effects of pH and ionic compound (i.e., NaCl) concentration upon the surface lubricity and surface defects (i.e., surface cracking).

In-Package-Crosslinking (IPC) Saline

IPC salines are prepared from the aqueous solutions prepared above that includes the formed water-soluble thermally-crosslinkable polymeric material by adding NaCl to have a concentration of about 0.79 w/w %. The pH of IPC saline is adjusted to a targeted value by adding either 1N NaOH. 5 ppm hydrogen peroxide may be added to the final IPC saline to prevent bioburden growth and the IPC saline is filtered using a 0.22 micron membrane filter.

SiHy Lenses with Hydrogel Top Coating

PAA-coated SiHy lenses obtained in Example 2 are placed in polypropylene lens packaging shells (or blisters) (one lens per shell) with 0.65 mL of a IPC saline (half of the saline is added prior to inserting the lens). The blisters are then sealed with foil and autoclaved for about 45 minutes at about 121° C., forming SiHy contact lenses with hydrogel top coatings (PAA-x-hydrophilic polymeric material) thereon.

The friction rating of resultant SiHy lenses are evaluated according to the procedures described in Example 1; and the surface cracking of the resultant SiHy lenses are determined according to the procedures described in Example 1. The results are reported in Table 3 and Table 4.

TABLE 3

| IPC agent Preparation | | | | Friction | Surface Cracking Method 2 | |
|---|---|---|---|---|---|---|
| pH | [NaCl] mM | Rxn T (° C.) | Rxn t (hrs) | Rating | Part I | Part II |
| 8.0 | 135 | 65 | 6 | 1, 0, 1 | 1, 1, 1 | 0, 0, 0 |
| 7.4 | 68 | 65 | 6 | 0, 0, 0 | 0, 0, 0 | 0, 0, 0 |

* [PAE] = 0.12 w/w %; [poly(AAm-co-AA)] = 0.13 w/w %; [NaH$_2$PO$_4$] = 3.2 mM; [Na$_2$HPO$_4$] = 12.9 mM.

TABLE 4

| IPC agent Preparation | | | Friction | Surface Cracking Method 2 | |
|---|---|---|---|---|---|
| pH | [PAE] w/w % | [poly(AAm-co-AA)] w/w % | Rating | Part I | Part II |
| 9.0 | 0.088 | 0.07 | 0, 0, 0 | 0, 0, 0 | 3, 2, 3 |
| 10.0 | 0.088 | 0.07 | 0, 0, 0 | 0, 0, 0 | 1, 0, 0 |
| 9.0 | 0.12 | 0.13 | 0, 0, 0 | 0, 0, 0 | 0, 0, 0 |
| 10.0 | 0.12 | 0.13 | 0, 0, 0 | 0, 0, 0 | 0, 0, 0 |
| 7.4 | 0.12 | 0.13 | 0, 0, 0 | 0, 1, 3 | 0, 1, 3 |

* [NaCl] = 135 mM; [NaH$_2$PO$_4$] = 3.2 mM; [Na$_2$HPO$_4$] = 12.9 mM; Rxn temperature = 65° C.; Rxn time = 6 hours.

The results show that no surface cracking is observed from lenses coated with IPC saline with 68 mM NaCl while lenses coated with pre-reaction pH at 8.0 shows light cracking (S.C. rating=1); and that as the pH of the reaction solution increases from 7.4 to 10.0, superior lubricity can be achieved while minimizing surface cracking.

Example 6

Preparation of IPC Saline

A water-soluble thermally-crosslinkable polymeric material (i.e., IPC agent" is prepared from polyamidoamine-epichlorohydrin (PAE) and poly(acrylamide-co-N-(3-Aminopropyl)methacrylamide)(92/8 w/w) (i.e., PAAm-APMAm). PAE solutions of different solid contents (Kymene) are purchased from Ashland as an aqueous solution and used as received. PAAm-APMAm (92/8 w/w), was synthesized in-house (amine functionality ~0.44 meq/g, an aqueous solution with solid content ~2.36%). The preparation steps are: (1) dissolve phosphate salts (~26 mM), poly(AAm-co-APMAm), PAE, and water (the concentration of poly(AAm-co-APMAm) and PAE are about 10 times of the concentration of the IPC agent in the final IPC saline). (2) Adjust pH to ~9.2 by 1N NaOH (about 0.488 gram of 1N NaOH, i.e., about 23 mM), (3) react the mixture in a water bath at temperature=70° C. for 3 hours, (4) remove the mixture from water bath and cool down in a room temperature water bath, (5) add proper amount of NaCl (0.79 wt %) to the mixture after it cooled down, (6) dilute the mixture with PBS buffer and adjust pH to ~7.3. (7) filter the mixture by 0.22 μm PES sterile filter unit. The detailed composition is shown below:

| IPC Agent Preparation | | | | | | | |
|---|---|---|---|---|---|---|---|
| PAAm-APMAm in step 1 (gram) | Water in step 1 (gram) | NaH$_2$PO$_4$•H$_2$O in step 1 (gram) | Na$_2$HPO$_4$•2H$_2$O in step 1 (gram) | PAE in step 1 (gram) | NaCl in step 5 (gram) | Finished mixture in step 5 (gram) | PBS saline (gram) |
| 11.6790 | 8.0641 | 0.0092 | 0.0815 | 1.0002 | 0.1659 | 20.00 | 180.00 |

| | Surface Cracking Method 2 | |
|---|---|---|
| Friction Rating | Part I | Part II |
| 0, 0, 0 | 0, 0, 0 | 0, 0, 0 |

Example 7

Preparation of IPC Saline

An IPC saline is prepared according to the process described in Example 6 except the the following modifications: add only PAAm-APMAm, PAE, and water in step 1 for reaction; adjust pH to ~8.6 in step 2 by ~0.67 gram of 1N NaOH (i.e., ~31 mM); add NaCl and phosphate salt in step 5.

The detail composition shown below:

| IPC Agent Preparation | | | | | | | |
|---|---|---|---|---|---|---|---|
| PAAm-APMAm in step 1 (gram) | Water in step 1 (gram) | NaH$_2$PO$_4$•H$_2$O in step 5 (gram) | Na$_2$HPO$_4$•2H$_2$O in step 5 (gram) | PAE in step 1 (gram) | NaCl in step 5 (gram) | Finished mixture in step 5 (gram) | PBS saline (gram) |
| 11.6790 | 8.0641 | 0.0092 | 0.0815 | 1.0002 | 0.1659 | 20.00 | 180.00 |

| | Surface Cracking Method 2 | |
|---|---|---|
| Friction Rating | Part I | Part II |
| 2, 2, 2 | 1, 1, 1 | 1, 1, 1 |

Example 8

Preparation of IPC Saline

An IPC saline is prepared according to the process described in Example 6 except that the concentration of PAAm-APMAm, and PAE are 15 times of final saline and the pH is adjusted to ~9.0 in step 2.

The detail composition shown below:

| IPC Agent Preparation | | | | | | | |
|---|---|---|---|---|---|---|---|
| PAAm-APMAm in step 1 (gram) | Water in step 1 (gram) | NaH$_2$PO$_4$•H$_2$O in step 1 (gram) | Na$_2$HPO$_4$•2H$_2$O in step 1 (gram) | PAE in step 1 (gram) | NaCl in step 5 (gram) | Finished mixture in step 5 (gram) | PBS saline (gram) |
| 17.5185 | 1.7245 | 0.0092 | 0.0815 | 1.5003 | 0.1659 | 13.33 | 186.67 |

| | Surface Cracking Method 2 | |
|---|---|---|
| Friction Rating | Part I | Part II |
| 0, 0, 0 | 0, 0, 0 | 0, 0, 0 |

Example 9

Preparation of IPC Saline

An IPC saline is prepared according to the process described in Example 6 except that the concentration of PAAm-APMAm, and PAE are 30 times of final saline, a powder form of in-house PAAm-APMAm is used, and the pH is adjusted to 9.0 in step 2.

The detail composition shown below:

| IPC Agent Preparation | | | | | | | |
|---|---|---|---|---|---|---|---|
| PAAm-APMAm in step 1 (gram) | Water in step 1 (gram) | $NaH_2PO_4 \cdot H_2O$ in step 1 (gram) | $Na_2HPO_4 \cdot 2H_2O$ in step 1 (gram) | PAE in step 1 (gram) | NaCl in step 5 (gram) | Finished mixture in step 5 (gram) | PBS saline (gram) |
| 0.5906 | 12.0827 | 0.0066 | 0.0582 | 2.1433 | 0.1185 | Gelled | N/A |

The reaction mixture was gelled indicating the crosslinking reaction rate increased dramatically at high reactant concentration and elevated pH.

Example 10

Preparation of IPC Saline

An IPC saline is prepared according to the process described in Example 6 except: add only PAAm-APMAm, PAE, and water in step 1; adjust pH to ~9.3 in step 2 for one mixture, and to ~10.3 for the other; and add NaCl and phosphate salt in step 5.

The detail composition shown below:

| IPC Agent Preparation pH before reaction (1N NaOH to adjust) in step 2 | Friction Rating | Surface Cracking Method 2 | |
|---|---|---|---|
| | | Part I | Part II |
| 9.3 | 0, 0, 0 | 0, 0, 0 | 1, 1, 0 |
| 10.3 | 0, 0, 0 | 0, 0, 0 | 0, 0, 0 |

What is claimed is:

1. A method for producing a water-soluble thermally-crosslinkable polymeric material, comprising the steps of:
   (1) obtaining a reactive mixture which is an aqueous solution comprising
      (a) an azetidinium-containing polymer having azetidinium groups, wherein the azetidinium-containing polymer is a poly(2-oxazoline-co-ethyleneimine)-epichlorohydrin,
      (b) a hydrophilicity-enhancing agent having at least one reactive functional group selected from the group consisting of primary amino group, secondary amino group, carboxyl group, thiol group, and a combination thereof, and
      (c) one or more non-polymeric ionic compounds, provided that the aqueous solution either has a pH of at least 8.0 and/or that the non-polymeric ionic compounds are present in the aqueous solution in a total amount of (i) 0 mM to about 135 mM if the hydrophilicity-enhancing agent is non-ionic or positively-charged at the pH of the aqueous solution or (ii) from about 20 millimolars (mM) to about 135 mM if the hydrophilicity-enhancing agent is negatively-charged at the pH of the aqueous solution; and
   (2) heating the reactive mixture to reach a reaction temperature of from about 40° C. to about 85° C. and maintaining the temperature of the reactive mixture at the reaction temperature for a time period sufficient to obtain the water-soluble thermally-crosslinkable polymeric material in which the hydrophilicity-enhancing agent is covalently attached to the azetidinium-containing polymer through one or more covalent linkages each formed between one azetidinium group and one reactive functional group,
   wherein the water-soluble thermally-crosslinkable polymeric material comprises azetidinium groups.

2. The method of claim 1, wherein the reactive mixture comprises from 0.01% to about 10% by weight of the azetidinium-containing polymer and from about 0.01% to about 10% by weight of the hydrophilicity-enhancing agent having at least one reactive function group, provided that the concentration ratio of the azetidinium-containing polymer to the hydrophilicity-enhancing agent in the reactive mixture is from about 1000:1 to 1:1000.

3. The method of claim 1, wherein the hydrophilicity-enhancing agent is: a polyethylene glycol having one sole primary or secondary amino, carboxyl, or thiol group; a polyethylene glycol with two terminal primary or secondary amino, carboxyl, and/or thiol groups; a multi-arm polyethylene glycol with one or more primary or secondary amino, carboxyl, and/or thiol groups; a polyethylene glycol dendrimer with one or more primary or secondary amino, carboxyl, and/or thiol groups.

4. The method of claim 1, wherein the hydrophilicity-enhancing agent is a copolymer which is a polymerization product of a composition comprising (1) about 60% or less by weight of one or more reactive vinylic monomers and (2) one or more non-reactive hydrophilic vinylic monomers.

5. The method of claim 4, wherein said one or more reactive vinylic monomers are vinylic monomers having a carboxyl group.

6. The method of claim 5, wherein said one or more reactive vinylic monomers are selected from the group consisting of acrylic acid, $C_1$-$C_4$ alkylacrylic acid, N-2-(meth)acrylamidoglycolic acid, beta methyl-acrylic acid (crotonic acid), alpha-phenyl acrylic acid, beta-acryloxy propionic acid, sorbic acid, angelic acid, cinnamic acid, 1-carboxy-4-phenyl butadiene-1,3, itaconic acid, citraconic acid, mesaconic acid, glutaconic acid, aconitic acid, maleic acid, fumaric acid, tricarboxy ethylene, and combinations thereof.

7. The method of claim 5, wherein said one or more reactive vinylic monomers are acrylic acid, methylacrylic acid, or combinations thereof.

8. The method of claim 4, wherein said one or more reactive vinylic monomers are vinylic monomers having a primary or secondary amino group.

9. The method of claim 8, wherein said one or more reactive vinylic monomers are amino-$C_2$-$C_6$ alkyl (meth)acrylate, $C_1$-$C_6$ alkylamino-$C_2$-$C_6$ alkyl (meth)acrylate, allylamine, vinylamine, amino-$C_2$-$C_6$ alkyl (meth)acrylamide, $C_1$-$C_6$ alkylamino-$C_2$-$C_6$ alkyl (meth)acrylamide, and combinations thereof.

10. The method of claim 4, wherein said one or more non-reactive vinylic monomers are selected from the group consisting of (meth)acrylamide, N,N-dimethyl (meth)acrylamide, N-vinylpyrrolidone (NVP), N-vinyl formamide, N-vinyl acetamide, N-vinyl isopropylamide, N-vinyl-N-methyl acetamide, N,N-dimethylaminoethyl (meth)acrylate, N,N-dimethylaminopropyl (meth)acrylamide, glycerol (meth)acrylate, 3-(meth)acryloylamino-1-propanol, N-hydroxyethyl (meth)acrylamide, N-hydroxypropyl (meth)acrylamide, N-[tris(hydroxymethyl)methyl]-acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 2-hydroxyethyl (meth)acrylate, hydroxypropyl (meth)acrylate, $C_1$-$C_4$-alkoxy polyethylene glycol (meth)acrylate having a weight average molecular weight of up to 1500 Daltons, allyl alcohol, vinyl alcohol, and combinations thereof.

11. The method of claim 4, wherein said one or more non-reactive vinylic monomers are phosphorylcholine-containing vinylic monomers.

12. The method of claim 4, wherein said one or more non-reactive vinylic monomers are methacryloyloxyethyl phosphorylcholine.

13. The method of claim 4, wherein said one or more non-reactive vinylic monomers are selected from the group consisting of acryamide, N,N-dimethylacrylamide, N-vinylpyrrolidone, (meth)acryloyloxyethyl phosphorylcholine, N-vinyl-N-methyl acetamide, glycerol (meth)acrylate, hydroxyethyl (meth)acrylate, N-hydroxyethyl (meth)acrylamide, $C_1$-$C_4$-alkoxy polyethylene glycol (meth)acrylate having a weight average molecular weight of up to 400 Daltons, vinyl alcohol, and combination thereof.

14. The method of claim 1, wherein the hydrophilicity-enhancing agent is a primary or secondary amino- or carboxyl-containing polysaccharide, hyaluronic acid, chondroitin sulfate, and combinations thereof.

15. The method of claim 1, wherein the hydrophilicity-enhancing agent is a primary or secondary amino-containing monosaccharide, a carboxyl-containing monosaccharide, a thiol-containing monosaccharide, a primary or secondary amino-containing disaccharide, a carboxyl-containing disaccharide, a thiol-containing disaccharide, a primary or secondary amino-containing oligosaccharide, a carboxyl-containing oligosaccharide, a thiol-containing oligosaccharide, or a combination thereof.

16. The method of claim 1, wherein the concentrations of the hydrophilicity-enhancing agent and the azetidinium-containing polymer in the aqueous solution are at least about 10 times of a targeted concentration of the water-soluble thermal-crosslinkable polymeric material in a packaging solution to be used for forming a non-silicone hydrogel coating on a hydrogel contact lens or a medical device according to in-package-crosslinking (IPC) process.

* * * * *